US007807378B2

(12) United States Patent
Tseng et al.

(10) Patent No.: US 7,807,378 B2
(45) Date of Patent: Oct. 5, 2010

(54) METHOD OF DIAGNOSING MYASTHENIA GRAVIS AND KITS THEREFOR

(75) Inventors: Tzu-Ling Tseng, Chiayi (TW); Pei-Hsiu Liao, Taipei (TW); Ping-Fu Cheng, Chenggong Village (TW); Shih-Feng Tsai, Jhunan Township, Miaoli County (TW); Hou-Chang Chiu, Taipei (TW)

(73) Assignees: Industrial Technology Research Institute (ITRI), Hsinchu County (TW); National Health Research Institutes (NHRI), Miaoli County (TW); Shin Kong Wu Ho-Su Memorial Hospital, Taipei (TW)

( * ) Notice: Subject to any disclaimer, the term of this patent is extended or adjusted under 35 U.S.C. 154(b) by 0 days.

(21) Appl. No.: 11/321,516

(22) Filed: Dec. 29, 2005

(65) Prior Publication Data

US 2007/0154968 A1    Jul. 5, 2007

(51) Int. Cl.
   *G01N 33/53* (2006.01)
(52) U.S. Cl. .................. 435/7.1; 435/7.9; 435/7.92; 436/501; 436/518; 436/811
(58) Field of Classification Search ................. 435/7.1, 435/7.92–7.94; 436/63, 501, 506, 518, 811
   See application file for complete search history.

(56) References Cited

U.S. PATENT DOCUMENTS

| | | | |
|---|---|---|---|
| 4,033,722 A | 7/1977 | Lindstrom | |
| 4,789,640 A | 12/1988 | Lindstrom | |
| 5,578,496 A | 11/1996 | Atassi et al. | |
| 5,777,083 A | 7/1998 | Burnie et al. | |
| 2002/0081652 A1 | 6/2002 | Fuchs et al. | |
| 2003/0119064 A1* | 6/2003 | Valkirs et al. | 435/7.1 |
| 2004/0235045 A1 | 11/2004 | Nyland et al. | |
| 2004/0241744 A1* | 12/2004 | Kohno et al. | 435/7.1 |
| 2005/0124076 A1 | 6/2005 | Tseng et al. | |
| 2005/0260770 A1 | 11/2005 | Cohen et al. | |

FOREIGN PATENT DOCUMENTS

| | | |
|---|---|---|
| JP | 2004-4257862 | 9/2004 |
| WO | WO 03/070761 | 8/2003 |

OTHER PUBLICATIONS

Pashov et al., Autoantibodies to heat shock protein 90 in the human natural antibody repertoire, International Immunology, vol. 14, No. 5, pp. 453-461.*
Conroy et al., Detection of autoantibodies to the 90 kDa heat shock protein in Systemic Lupus Erythematosus and other autoimmune diseases, British Journal of Rheumatology 1994; 33: 923-926.*
Kim, Diagnostic significance of antibodes to heat shock proteins, Clinica Chimica Acta 337 (2003) pp. 1-10.*
Trieb et al., Antibodies to heat shock protein 90 in osteosarcoma patients correlate with response to neoadjuvant chemotherapy, British Journal of Cancer (2000) 82(1), 85-87.*
Kenderov et al. Lupus-specific kidney deposits of HSP90 are associated with altered IgG idiotipic interactions of anti-HSP90 autoantibodies, Clin Exp Immunol 2002; 129: 169-176.*
Joachim et al., Autoantibodies in patient with glaucoma: a comparison of IgG serum antibdoes against retinal, optic nerve, and optic nerve head antigens, Graefe's Arch Clin Exp Ophthalmol (2005) 243: 817-823.*
Quintana et al., Experimental autoimmune myasthenia gravis in naive non-obese diabetic (NOD/LtJ) mice: susceptibility associated with natural IgG antibodies to the acetylcholine receptor, International Immunology, vol. 15, No. 1, pp. 11-16.*
Partial European Search Report for European Patent Application No. 06290012.1-2404, mailed Oct. 23, 2006 (4 pages).
R. Astarloa and J.C. Martinez Castrillo, "Humoral response to the human heat shock 60 kDa protein in myasthenia gravis," J. Neurol. Sci. 135:182-183 (1996).
K. Yonekura et al., "Prevalence of anti-heat shock protein antibodies in cerebrospinal fluids of patients with Guillain-Barré syndrome," J. Neuroimmunol. 156:204-209 (2004).
Cotran et al., Pathologic Basis of Disease 211-212, 1289 (W.B. Saunders Co., Philadelphia, PA; 6th ed. 1999).
Hennekens et al., Epidemiology in Medicine 331-335 (1st Ed. 1987).
Hoch et al., "Auto-antibodies to the receptor tyrosine kinase MuSK in patients with myasthenia gravis without acetylcholine receptor antibodies," Nature Med. 7(3):365-368 (2001).
Howard, "Myasthenia gravis: a summary," available at http://www.myasthenia.org/information/summary.htm (last accessed Oct. 23, 2005).
Kirkegaard & Perry Laboratories, Inc., Technical Guide for ELISA 9-21 (2003), available at http://www.kpl.com/home.cfm# (last accessed Nov. 3, 2005).
Luo et al., "Regulation of AChR clustering by dishevelled interacting with MuSK and PAK1," Neuron 35:489-505 (2002).
Morgan et al., "The Matrix Effects on Kinetic Rate Constants of Antibody-Antigen Interactions Reflect Solvent Viscosity," J. Immunol. Meth. 217:51-60 (1998).
"Myasthenia Gravis," available at http://www.neuroland.com/nm/myas_gra.htm (last accessed Dec. 1, 2005).
Osserman, K.E. et al., "Studies in myasthenia gravis: review of a twenty-year experience in over 1200 patients," Mt. Sinai J. Med. 38(6):497-537 (1971).
Parsell et al., "The function of heat-shock proteins in stress tolerance: degradation and reactivation of damaged proteins," Ann Rev. Genet. 27:437-496 (1993).

(Continued)

*Primary Examiner*—Melanie Yu
*Assistant Examiner*—Gary W Counts
(74) *Attorney, Agent, or Firm*—Finnegan, Henderson, Farabow, Garrett & Dunner, L.L.P.

(57) ABSTRACT

The present invention relates to methods of diagnosing myasthenia gravis in a subject, by determining an amount of at least one autoantibody that specifically binds one or more autoantigens selected from heat-shock protein 60 (hsp60), heat-shock protein 90, alpha isoform (hsp90α), and heat-shock protein 90, beta isoform (hsp90β). The invention also provides diagnostic kits for identifying a subject having myasthenia gravis.

11 Claims, 5 Drawing Sheets

OTHER PUBLICATIONS

Ragheb et al., "Myasthenia gravis patients, but not healthy subjects, recognize epitopes that are unique to the ε-subunit of the acetylcholine receptor," *J. Neuroimmunol.* 159:137-145 (2005).

Richman et al., "Treatment of autoimmune myasthenia gravis," *Neurol.* 61:1652-1661 (2003).

Robinson et al., "Autoantigen microarrays for multiplex characterization of autoantibody responses," *Nature Med.* 8(3):295-301 (2002).

Roxanis et al., "Thymic myoid cells and germinal center formation in myasthenia gravis; possible roles in pathogenesis," *J. Neuroimmunol.* 125:185-197 (2002).

Sambrook et al., 3 Molecular Cloning: A Laboratory Manual A8.40-A8.45 and A8.52-A8.55 (Cold Spring Harbor Laboratories Press, Cold Spring Harbor, NY, 3d ed. 2001).

Scofield, "Autoantibodies as predictors of disease," *Lancet* 363:1544-1546 (2004).

Somnier, "Increasing incidence of late-onset anti-AChR antibody-seropositive myasthenia gravis," *Neurol.* 65:928-930 (2005).

Sreedhar et al., "Hsp90 isoforms: functions, expression and clinical importance," *FEBS Letters* 562:11-15 (2004).

Zhuang et al., "Measurement of Association Rate Constant of Antibody-Antigen Interaction in Solution Based on Enzyme-Linked Immunosorbent Assay," *J. Biosci. Bioeng.* 92(4):330-336 (2001).

European Search Report for European Patent Application No. 06290012.1 mailed Oct. 1, 2007.

European Search Opinion for European Patent Application No. 06290012.1 mailed Oct. 1, 2007.

D.B. Jones et al., "Sequence homologies between hsp 60 and autoantigens," Immunology Today, vol. 14, pp. 115-118 (1993).

S.E. Conroy et al., "Incidence of anti Hsp 90 and 70 antibodies in children with SLE, juvenile dermatomyositis and juvenile chronic arthritis," Clin. Exp. Rheum. vol. 14, pp. 99-104 (1996).

S.E. Conroy et al., "Detection of antibodies to the 90kDa heat shock protein in patients with SLE and other autoimmune rheumatic diseases," Arthritis and Rheumatism, vol. 36, p. S236 (1993).

S. Minota et al., "Autoantibodies to the heat-shock protein hsp90 in systemic Lupus Erythematosus," Journal of Clinical Investigation, vol. 81, pp. 106-109 (1988).

Pashov et al., Autoantibodies to heat shock protein 90 in the human natural antibody repertoire, International Immunology, vol. 14, No. 5, pp. 453-461, 2002.

Conroy et al., Detection of autoantibodies to the 90 kDa heat shock protein in Systemic Lupus Erythematosus and other autoimmune diseases, British Journal of Rheumatology 1994; 33: 923-926.

Kim, Diagnostic significance of antibodes to heat shock proteins, Clinica Chimica Acta 337 (2003) pp. 1-10.

Trieb et al., Antibodies to heat shock protein 90 in osteosarcoma patients correlate with response to neoadjuvant chemotherapy, British Journal of Cancer (2000) 82(1), 85-87.

Kenderov et al. Lupus-specific kidney deposits of HSP90 are associated with altered IgG idiotipic interactions of anti-HSP90 autoantibodies, Clin Exp Immunol 2002; 129: 169-176.

Joachim et al., Autoantibodies in patient with glaucoma: a comparison of IgG serum antibdoes against retinal, optic nerve, and optic nerve head antigens, Graefe's Arch Clin Exp Ophthalmol (2005) 243: 817-823.

Quintana et al., Experimental autoimmune myasthenia gravis in naive non-obese diabetic (Nod/LtJ) mice: susceptibility associated with natural IgG antibodies to the acetylcholine receptor, International Immunology, vol. 15, No. 1, pp. 11-16, 2003.

\* cited by examiner

HF

HM

TF

TM

HF

HM

TF

TM

HF

HM

TF

TM

HF

HM

TF

TM

METHOD OF DIAGNOSING MYASTHENIA GRAVIS AND KITS THEREFOR

DESCRIPTION OF THE INVENTION

1. Field of the Invention

The invention relates to the field of immunology, including the development of immunological tolerance, and the pathology of autoimmune disorders. The invention generally relates to improved methods of diagnosing the organ-specific autoimmune disease myasthenia gravis.

2. Background of the Invention

Autoimmune diseases result from aberrant immune cell function or activity which causes inappropriately activated T cells to react against self tissue, thereby triggering production of cytokines and/or autoantibodies responsible for disease etiology and progression. COTRAN ET AL., PATHOLOGIC BASIS OF DISEASE 211-212 (6th ed. 1999); Scofield, "Autoantibodies as predictors of disease," *Lancet* 363:1544-1546 (2004). Autoimmunity indicates a loss of self-tolerance, though the mechanisms by which this occurs are not fully understood. Id. Autoimmune disorders may be systemic, affecting multiple organs or tissues, or localized, affecting a single organ, organ system or tissue. Id.

A hallmark of autoimmune disease is the production of high affinity autoantibodies directed against self proteins. Robinson et al., "Autoantigen microarrays for multiplex characterization of autoantibody responses," *Nature Med.* 8(3): 295-301 (2002). Some autoantibodies are known or strongly suspected to be involved in the development of cell and tissue damage associated with a particular disease, but for most, neither the pathogenic role nor the relationship to the underlying etiology of disease is known. Id. Nevertheless, the specificity and pathogenicity of autoantibody responses for certain diseases, such as myasthenia gravis, emphasizes their utility in improving diagnosis, classification, and treatment of autoimmune disorders. Id. Because serum autoantibodies often appear long before the onset of clinical symptoms, the ability to detect autoantibodies associated with specific autoimmune disorders quickly and accurately would enable the use of prophylactic treatments earlier in the course of disease, and may eventually permit immunological intervention sufficient to prevent the onset of disease entirely. Scofield, supra.

Myasthenia gravis ("MG") is a neuromuscular disorder caused by immune-mediated loss of acetylcholine receptors at neuromuscular junctions of skeletal muscle. Cotran et al., supra at 1289. Estimates of the incidence of MG in populations worldwide range from approximately three to more than twenty people per 100,000. Cotran et al., supra; Somnier, "Increasing evidence of late-onset anti-AChR antibody-seropositive myasthenia gravis," *Neurol.* 65:928-930 (2005). The prevalence of MG in the United States is estimated at about fourteen cases per 100,000 people, with approximately 36,000 cases diagnosed annually nationwide. Howard, "Myasthenia gravis: a summary."

Early onset myasthenia gravis, defined as arising either before age 40, or before age 50, tends primarily to appear in women, but late onset MG afflicts men and women equally. COTRAN ET AL., supra (noting that MG is most commonly observed in women "[w]hen arising before age 40 years"); Somnier, supra ("the dichotomy between early- and late-onset MG was defined at age 50"). Women typically develop the disease between the ages of twenty and forty, while in men, it generally appears between the ages of fifty and sixty, though it sometimes develops earlier, and may develop later in both sexes. COTRAN ET AL., supra.

Clinically, MG typically appears first as occasional muscle weakness in approximately two-thirds of patients, most commonly in the extraocular muscles. Id.; Howard, supra. These initial symptoms eventually worsen, producing drooping eyelids (ptosis) and/or double vision (diplopia), often causing the patient to seek medical attention. Id. Muscle weakness is restricted to the ocular muscles in about 10% of cases. Howard, supra. Eventually, many patients develop general muscular weakness that may fluctuate weekly, daily, or even more frequently. Id. Generalized MG often affects muscles that control facial expression, chewing, talking, swallowing, and breathing; before recent advances in treatment, respiratory failure was the most common cause of death. Id. With improved methods of treatment and critical care intervention, however, more than 95% of patients now survive for five years or more after diagnosis. Id. MG is frequently accompanied by thymic hyperplasia, observed in approximately 65% of patients, or, less commonly by thymoma, observed in about 15% of patients. Id.

Long-term outcome of MG patients has improved with more effective use of cholinesterase inhibitors and improved critical care, but therapies that directly reduce the autoimmune response or modify its effects on acetylcholine receptors and the surrounding neuromuscular junction may prove more effective in the long term. Richman et al., "Treatment of autoimmune myasthenia gravis," *Neurol.* 61:1652-1661 (2003). Treatment usually begins with the administration of anticholinesterase agents, including cholinesterase inhibitors. Id. Treatment regimes generally aim to induce immunologic remission with high doses of corticosteroids, frequently in conjunction with intravenous immunoglobulin or plasmapheresis. Id. Maintenance of remission is usually accomplished by gradual tapering of the corticosteroids, coupled with the use of "steroid-sparing" agents, such as azathioprine or mycophenolate. Id. Thymectomy may also be effective in some cases. Id.

MG is characterized by antibodies directed against the nicotinic acetylcholine receptor (AChR) in approximately 80-85% of patients. Richman et al., supra; Roxanis et al., "Thymic myoid cells and germinal center formation in myasthenia gravis; possible roles in pathogenesis," *J. Neuroimmunol.* 125:185-197 (2002). These antibodies cause loss of acetylcholine receptors and diminished receptor function at the muscle end-plate of the mature neuromuscular junction, which together lead to failure of neuromuscular signal transmission that manifests as the muscle weakness characteristic of generalized MG. Hoch et al., "Auto-antibodies to the receptor tyrosine kinase MsSK in patients with myasthenia gravis without acetylcholine receptor antibodies," *Nature Med.* 7(3):365-368 (2001). The serum concentration of anti-AChR antibodies varies widely among patients with similar degrees of muscular weakness, and therefore cannot be used to predict severity of the disease in individual patients. Howard, supra.

Not every patient with symptoms of generalized MG develops anti-AChR antibodies, however. Roxanis et al., supra. In some cases, symptomatic patients lack detectable anti-AChR antibodies until several months after onset of symptoms, or even longer. Id. Anti-AChR antibodies are observed more frequently in patients afflicted with generalized MG compared to those suffering only from ocular MG: approximately 74% of those with generalized MG, and 54% of those with ocular MG have detectable anti-AChR antibody in serum. Howard, supra. Another 10-20% of patients suffering from generalized MG never develop detectable anti-AChR antibodies, though as many as 90% of patients lacking anti-AChR antibodies instead have serum auto-antibodies directed to a muscle-specific receptor tyrosine kinase, MuSK. Hoch et al., supra; Roxanis et al., supra. MuSK mediates agrin-induced clustering of AChRs during synapse formation, and is expressed at the mature neuromuscular junction. Hoch et al., supra.

Thus, there remains a need for additional methods of diagnosing the disease.

SUMMARY OF THE INVENTION

The present invention provides methods for diagnosing the neuromuscular autoimmune disorder myasthenia gravis ("MG"). The invention is based at least in part on the discovery that many patients suffering from early stages of MG have autoantibodies specific for the 60 kD heat-shock protein ("hsp60") and the 90 kD heat-shock protein ("hsp90"), two proteins not previously associated with the etiology and progression of MG. Accordingly, the invention provides a method of diagnosing MG in a subject comprising obtaining a biological sample from the subject and determining an amount of at least one autoantibody that specifically binds an autoantigen characteristic of MG selected from heat-shock protein 60 (hsp60) (SEQ ID NO:1), heat-shock protein 90, alpha isoform (hsp90α) (SEQ ID NO:2), and heat-shock protein 90, beta isoform (hsp90β) (SEQ ID NO:3).

An amount of an autoantibody may be determined by a variety of qualitative and quantitative methods. In some embodiments of the invention, an amount of an autoantibody is detected by Western blot. In other embodiments, an amount of an autoantibody is detected by enzyme-linked immunosorbent assays.

In another aspect, the invention provides a diagnostic kit to implement the method of the invention. The kits of the invention incorporate one or more of the above techniques for determining an amount of at least one autoantibody that specifically binds an autoantigen characteristic of MG. In one aspect, the kit includes all reagents required to determine an amount of at least one autoantibody that specifically binds an autoantigen selected from heat-shock protein 60 (hsp60) (SEQ ID NO:1), heat-shock protein 90, alpha isoform (hsp90α) (SEQ ID NO:2), and heat-shock protein 90, beta isoform (hsp90β) (SEQ ID NO:3).

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

Figure 1:
FIG. 1 shows Western blots of cell lysates probed with serum from patients suffering from generalized myasthenia gravis according to the protocol of Example 1, identifying autoantibodies specific for heat-shock protein 60 (hsp60). Positive blots are indicated with a dot. Samples were taken from female patients with thymic hyperplasia (HF), male patients with thymic hyperplasia (HM), female patients with thymoma (TF), and male patients with thymoma (TM).
Figure 1:
Figure 1:
Figure 1:
Figure 1:
Figure 1:
Figure 1:
Figure 1:

Table 1 shows that patients with stage I or stage IIa MG who lack AChR autoantibodies exhibit hsp60 or hsp90 autoantibodies as measured by ELISAs.

Table 2 compares the diagnostic sensitivity of assays specific for (1) AChR; (2) hsp60; (3) hsp90; (4) hsp60+hsp90; (5) AChR+hsp60; or (6) AChR+hsp90. Assaying for autoantibodies specific for AChR alone exhibited the lowest sensitivity for patients having stage I (ocular) MG.

BRIEF DESCRIPTION OF THE SEQUENCES

SEQ ID NO:1 is the amino acid sequence of human heat-shock protein 60 (hsp60).

SEQ ID NO:2 is the amino acid sequence of human heat-shock protein 90, alpha isoform (hsp90α).

SEQ ID NO:3 is the amino acid sequence of human heat-shock protein 90, beta isoform (hsp90β).

DETAILED DESCRIPTION OF THE INVENTION

I. Method of Diagnosing Autoimmune Disorders

In one aspect, the invention provides methods of diagnosing myasthenia gravis in a subject, comprising obtaining a biological sample from a subject, and determining an amount of at least one autoantibody, wherein the autoantibody specifically binds at least one protein selected from heat-shock protein 60 (hsp60), heat-shock protein 90, alpha isoform (hsp90α), and heat-shock protein 90, beta isoform (hsp90β).

An autoimmune disorder is a disease or disorder characterized by aberrant immune function, and frequently by the presence of autoantibodies. An autoantibody is an immunoglobulin protein ("Ig," also referred to as an "antibody") of any isotype, including $IgG_1$, $IgG_2$, $IgG_3$, $IgG_4$, $IgA_1$, $IgA_2$, IgD, IgE, or IgM, that specifically binds a target antigen derived from a protein produced by the same organism that produced the Ig protein, or antibody. Examples of autoimmune disorders characterized by autoantibodies include: Addison's disease (autoantibodies against 21-hydroxylase); coeliac disease (autoantibodies against tissue transglutaminase); type 1 insulin-dependent diabetes mellitus (autoantibodies against GAD-65 and/or insulin); Graves' disease/hyperthyroidism (autoantibodies against thyroid-stimulating-hormone receptor); Hashimoto's thyroiditis (autoantibodies against thyroid peroxidase and/or thyroglobulin); myasthenia gravis (autoantibodies against nicotinic acetylcholine receptor and/or muscle-specific receptor tyrosine kinase); Goodpasture's syndrome (autoantibodies against Type IV collagen in glomerular basement membranes); pemphigus vulgaris (autoantibodies against desmoglein 3); pernicious anemia (autoantibodies against H/K ATPase); primary biliary cirrhosis (autoantibodies against E2 PDS); vitiligo (autoantibodies against tyrosinase and/or SOX-10); multiple sclerosis (autoantibodies against myelin basic protein and/or myelin oligodendritic glycoprotein); systemic lupus erythematosus (autoantibodies against spliceosomal snRNP, Ro/La ribonuclear particle, histones, and/or native DNA); Sjögren's syndrome (autoantibodies against Ro/La ribonuclear particle and/or muscarinic receptor); and rheumatoid arthritis (autoantibodies against citrillunated cyclic peptide and/or IgM). Scofield, supra, at 1545.

"Subject", as used herein, means an animal, including a human or non-human mammal, e.g., a dog, a cat, a mouse, a rat, a cow, a sheep, a pig, a goat, or a non-human primate, and expressly includes laboratory mammals, livestock, and domestic mammals. In some embodiments, the mammal may be a human; in others, the mammal may be a rodent, such as a mouse or a rat.

A biological sample is any biological material collected from cells, tissues, or organs of the subject. The source of the biological sample may vary depending on the particular symptoms present in the subject to be diagnosed. The biological sample may be analyzed immediately after it is taken, or stored. If stored, the sample may be equilibrated with an appropriate storage buffer, and kept at 4° C., at −20° C., at −70° C., or even in cryogenic liquids, such as liquid nitrogen or liquid helium. In one embodiment, the biological sample may consist of blood, serum, or plasma. In another embodiment, the biological sample may consist of amniotic fluid or milk. In still another embodiment, the biological sample may consist of a biopsy or tissue sample, or a cell suspension. In additional embodiments of the invention, the biological sample may consist of saliva, cerebrospinal fluid, lymph, sweat, mucus, synovial fluid, lacrimal fluid, or other clinical specimens and samples.

The term "specifically binds," or the like, means that two molecules form a complex that is relatively stable under physiologic conditions (e.g., a stable antigen/antibody complex). The term is also applicable where, for example, an antigen-binding domain is specific for a particular epitope, which is found on a number of molecules. Thus, an antibody may specifically bind multiple proteins when it binds to an epitope present in each. Specific binding is characterized by a selective interaction, often including high affinity binding with a low to moderate capacity. Nonspecific binding usually is a less selective interaction, and may have a low affinity with a moderate to high capacity. Typically, binding is considered specific when the affinity is at least $10^5 M^{-1}$, $10^6 M^{-1}$, $10^7 M^{-1}$ or $10^8 M^{-1}$. If necessary, non-specific binding can be reduced without substantially affecting specific binding by varying the binding conditions. Such conditions are known in the art, and a skilled artisan using routine techniques can select appropriate conditions. The conditions are usually defined in terms of concentration of antibodies, ionic strength of the solution, temperature, time allowed for binding, concentration of non-related molecules (e.g., blocking agents such as serum albumin, milk casein), and so forth. See, e.g., Morgan et al., "The Matrix Effects on Kinetic Rate Constants of Antibody-Antigen Interactions Reflect Solvent Viscosity," *J. Immunol. Meth.* 217:51-60 (1998); and Zhuang et al., "Measurement of Association Rate Constant of Antibody-Antigen Interaction in Solution Based on Enzyme-Linked Immunosorbent Assay," *J. Biosci. Bioeng.* 92(4):330-336 (2001).

A. Detection of Autoantibodies

Determining an amount of an autoantibody according to the methods of the invention encompasses both qualitative and quantitative methods of detection. A qualitative method of detection simply determines whether a particular autoantibody is present in a biological sample. A quantitative method of detection determines both whether a particular autoantibody is present in a biological sample, and in what quantity. Both qualitative and quantitative methods of detection are well known in the art. Such methods include Western blotting, immunoblotting, immunofluorescence, enzyme-linked immunosorbent assays ("ELISA"), and other comparable techniques.

1. Western Blotting

Western blotting begins with an electrophoresis step, where proteins of interest are separated on the basis of size and charge by polyacrylamide gel electrophoresis, followed by transfer of the proteins from the gel to a charged membrane. After the transfer is completed, hybridization begins with a blocking step wherein all unreacted binding sites on the membrane are blocked to suppress nonspecific adsorption of antibodies, continues with a primary antibody incubation to bind a target antigen or antigens, and ends with a secondary antibody incubation wherein the antigen-antibody complex formed during the primary incubation is detected by radiographic, chromogenic, or chemiluminescent means. The secondary antibody is generally specific for the constant region ("Fc") common to all immunoglobulin protein isotypes. Secondary antibody may be obtained from a variety of mammalian sources, including, but not limited to, rabbit, sheep, goat, mouse, and rat.

To determine an amount of an autoantibody specific for an autoantigen characteristic of MG by Western blotting, purified or recombinant preparations of one or more of the autoantigens characteristic of MG are first subjected to sodium dodecyl-sulfate polyacrylamide gel electrophoresis (SDS-PAGE), according to standard methods well-known in the art. See, e.g., SAMBROOK ET AL., 3 MOLECULAR CLONING: A LABORATORY MANUAL A8.40-A8.45 (2001) (describing various reagents and methods for electrophoresis of proteins by SDS-PAGE). The contents of the gel are then transferred to nitrocellulose, nylon, PVDF, or other membrane or filter suitable for fixation and Western blotting by standard methods equally well-known in the art. The transfer may be by immersion, semi-dry blotting, or by other comparable methods known in the art.

Alternatively, purified or recombinant preparations of one or more of the autoantigens may be spotted directly on nitrocellulose, nylon, polyvinylidene fluoride ("PVDF"), or other filter or membrane suitable for fixation and Western blotting. If purified or recombinant preparations of the desired autoantigens are not available, the autoantigens may be supplied in cell lysates or tissue homogenates prepared with standard methods known in the art.

Next, the filters or membranes are fixed to prevent loss of the target proteins during the several hybridization, washing, and staining steps comprising Western blotting. Fixation may be accomplished by heat, cross-linking with ultraviolet light, or by other comparable methods known in the art. See, e.g., SAMBROOK ET AL., 3 MOLECULAR CLONING: A LABORATORY MANUAL A8.52-A8.55 (describing various reagents and methods for immunoblotting and detection of antigen/antibody complexes).

Non-specific antibody binding sites on the fixed filter or membrane are blocked with buffered solutions (e.g., phosphate-buffered saline ("PBS") or the like) containing a blocking agent such as, for example, 0.5% (w/v) low-fat dry milk or 5% (w/v) bovine serum albumin ("BSA"). After blocking, the filter or membrane then undergoes the primary antibody incubation, during which it is incubated with a biological sample from a subject to be diagnosed for an autoimmune disorder.

After the primary antibody incubation, the filter or membrane is washed, and the presence of autoantibody-autoantigen complexes detected using a secondary antibody labeled with chromogenic, fluorogenic, or chemiluminescent means. Autoantibody-autoantigen complexes are then detected calorimetrically (e.g., with horseradish peroxidase and TMB), or by autoradiography (e.g., alkaline phosphatase). If detected colorimetrically, or by chemiluminescence, the amount of color or fluorescence may be measured using a luminometer, a spectrophotometer, or other similar instruments. If detected autoradiographically, the amount of bound antibody may be measured from the exposed x-ray film using a densitometer, or similar instrument. See, e.g., SAMBROOK ET AL., 3 MOLECULAR CLONING: A LABORATORY MANUAL A8.52-A8.55 (describing various reagents and methods for immunoblotting and detection of antigen/antibody complexes).

Secondary antibodies used in qualitative or quantitative methods of detection, whether polyclonal or monoclonal, may be labeled with a ligand (such as biotin) or a detectable marker (such as a fluorescent group or an enzyme) using conventional techniques. Suitable labels include fluorophores, chromophores, electron-dense reagents (e.g., silver or gold), enzymes, and ligands having specific binding partners. Enzymes such as horseradish peroxidase or alkaline phosphatase are typically detected by their activity. For example, horseradish peroxidase can be detected by its ability to convert tetramethylbenzidine ("TMB") to a blue pigment, quantifiable with a spectrophotometer. Other suitable ligands and/or detectable markers include biotin and avidin or streptavidin, IgG and protein A, and the numerous additional receptor-ligand couples known in the art. Other permutations and possibilities will be readily apparent to those of ordinary skill in the art, and are considered as equivalents within the scope of the instant invention.

In one embodiment of the invention, an amount of at least one autoantibody which specifically binds an autoantigen selected from heat-shock protein 60 (hsp60), heat-shock protein 90, alpha isoform (hsp90α), and heat-shock protein 90, beta isoform (hsp90β) is determined by Western blotting.

There are many common variations on the standard Western blotting protocol, including Far Western blots, as well as quantitative blotting methods and numerous others. One of ordinary skill in the art will select the appropriate protocol to use, depending on the autoantibody to be detected, the autoantigen to be used, the source of autoantigen and/or primary autoantibody used in the assay, and any other relevant experimental parameters. These and many other permutations and possibilities will be readily apparent to those of ordinary skill in the art, and are considered as equivalents within the scope of the instant invention.

2. Enzyme-Linked Immunosorbent Assay ("ELISA")

Some ELISA methods are qualitative, used to measure simply the presence or absence of a particular antigen or antibody, while others are quantitative, permitting accurate measurement of antigen or antibody concentration. Because they are easy to perform and readily automated, ELISAs are commonly used to screen large numbers of antibodies or antigens for a particular binding specificity.

An ELISA begins with an antigen adsorption step, where the target antigen or antigens are adsorbed to the wells of a microtiter plate. See, e.g., Kirkegaard & Perry Laboratories, Inc., Technical Guide for ELISA 9-13 (2003) (discussing types of microtiter plates for use in ELISAs, as well as methods and reagents for adsorbing proteins to such plates). The most commonly used adsorption buffers for antibodies are 50 mM Carbonate, pH-9.6; 10 mM Tris-HCl, pH-8.5; and 10 mM PBS, pH=7.2. These buffers work well for many proteins. If the target antigen or antigens are not readily adsorbed to the surface of the microtiter plate, plates with surfaces modified or derivatized to permit covalent linkage of proteins to their surface by a variety of chemical means are widely available from commercial suppliers. Time and temperature are the most important factors affecting the amount of protein adsorbed.

Once the wells of a microtiter plate are coated with the desired antigen or antigens, they are washed with a blocking buffer to block non-specific antibody binding and to minimize false positive results. See, e.g., id. at 13-14 (discussing methods and reagents for blocking microtiter plates). Commonly used blocking agents are either protein solutions, such as BSA (typically used at concentrations between 1% and 5% (w/v) in PBS, pH=7.0), non-fat dry milk, casein (the main protein component of non-fat dry milk) or caseinate (a more soluble version of casein, produced by partial digestion with sodium hydroxide), normal serum (typically used at concentrations between 1% and 5% (v/v)), and gelatin (normally used at concentrations between 1% and 5% (w/v)), or non-ionic detergents, such as Tween-20™ and Triton X-100™.

Commonly used washing reagents are selected for their ability to disrupt low affinity interactions between various reaction components that can affect the ability to detect specific antigen-antibody interactions. See, e.g., id. at 14-15 (discussing methods and reagents for washing microtiter plates). Wash solutions commonly contain a physiological buffer to prevent denaturation of antigens and their cognate antibodies, and to preserve enzyme activity. Buffers such as PBS, Tris-saline, or imidizole-buffered saline at neutral pH are widely used. Specific buffers are typically selected based on the method of detection to be employed in a particular assay. Wash buffers should also include non-ionic detergents such as Tween-20™, Triton X-100™ or the like, at concentrations of between 0.01% to 0.05% (v/v), in order to disrupt low-affinity, non-specific interactions between reaction components.

After the blocking step, the wells of the microtiter plate are washed, the adsorbed antigen then undergoes the primary antibody incubation, during which it is incubated with a biological sample from a subject to be diagnosed for an autoimmune disorder. After the primary antibody incubation, the wells are washed, and the presence of autoantibody-autoantigen complexes detected using a secondary antibody labeled with chromogenic (e.g., with horseradish peroxidase and TMB), fluorescent or chemiluminescent (e.g., alkaline phosphatase) means. See, e.g., id. at 15-21 (discussing antibody preparation and use, as well as commonly used detection molecules). The amount of color or fluorescence may be measured using a luminometer, a spectrophotometer, or other similar instruments.

There are many common variations on the standard ELISA protocol, including competitive ELISA, sandwich ELISA, and numerous others. One of ordinary skill in the art will select the appropriate protocol to use, depending on the antibody to be detected, the antigen to be used, the source of antigen and/or primary antibody used in the assay, and any other relevant experimental parameters. These and many other permutations and possibilities will be readily apparent to those of ordinary skill in the art, and are considered as equivalents within the scope of the instant invention.

B. Clinical Forms of Myasthenia Gravis

Adult myasthenic patients have been divided into four groups, as classified by Osserman and Genkins. Osserman, K. E. and Genkins, G., "Studies in myasthenia gravis: review of a twenty-year experience in over 1200 patients," Mt. Sinai J. Med. 38(6):497-537 (1971); Tuen, C., "Myasthenia Gravis." Approximately 20% of patients are diagnosed with Type I MG, 30% with Type IIA, 20% with Type IIB, 11% with Type III, and 9% with Type IV. The remaining 10% of cases are typically pediatric in origin. Osserman and Genkins, supra, at 502.

In Type I MG, or ocular MG, symptoms are generally confined to ocular muscles of one or both eyes. It is characterized by ptosis and diplopia, but if symptoms do not spread to other muscle groups within two years, this form of MG usually remains non-progressive. Only 55% of patients with this type of MG have autoantibodies specific for AChR. Osserman, K. E. and Genkins, G., supra at 501; Tuen, C., "Myasthenia Gravis."

In Type IIa MG, or mild, generalized MG, symptoms tend to develop slowly, sometimes beginning with the ocular muscles, but gradually spread to the skeletal and bulbar musculature. Respiratory muscles are usually not affected. About 80% of patients with MG of this type have autoantibodies specific for AChR. In Type IIb MG, or moderate, generalized MG, symptoms again develop slowly, frequently beginning with the ocular muscles, and gradually spread to skeletal and bulbar musculature. The symptoms are typically more severe than in patients with Type IIA MG, but again, the respiratory muscles are usually spared. Osserman, K. E. and Genkins, G., supra at 501-02; Tuen, C., "Myasthenia Gravis."

In Type III MG, or acute, fulminating MG, the disease is moderately severe or acute, with rapid onset of symptoms in skeletal and bulbar muscles, and early involvement of respiratory muscles. Patients with Type III MG frequently develop thymomas. Disease progression is usually complete within six months. Mortality is high in patients with Type III MG. Essentially 100% of patients with MG of this type have autoantibodies specific for AChR. Osserman, K. E. and Genkins, G., supra at 502; Tuen, C., "Myasthenia Gravis."

In Type IV MG, or late, severe MG, the disease becomes chronic and severe, typically more than two years after onset of Type I or II-like symptoms. Approximately 89% of patients with this type of MG have autoantibodies specific for AChR. Osserman, K. E. and Genkins, G., supra at 502; Tuen, C., "Myasthenia Gravis."

At least two types of thymic pathology are regularly observed in patients with MG. About 50% of patients display some degree of thymic hyperplasia. Approximately 15% of patients eventually develop thymoma. In some cases, MG may be treated successfully by thymectomy, which results in sustained improvement of symptoms in more than 50% of patients, though it is less effective in older patients. Osserman, K. E. and Genkins, G., supra at 515-23.

C. Autoantigens Associated with Myasthenia Gravis

Candidate autoantigens associated with particular autoimmune disorders may be identified by a variety of methods, including, for example, the method described in U.S. Patent Publication No. US-2005/0124076-A1, published on Jun. 9, 2005, which is incorporated herein by reference. According to this method, serum antibodies are purified from serum samples obtained from healthy individuals and from individuals afflicted with an autoimmune disorder of interest, such as MG. The purified immunoglobulins are covalently attached to a chromatographic medium and used to make an affinity column. A protein sample isolated from a subject having MG, for example, taken from an organ, tissue, or cell type involved in the etiology or progression of the disease, is then analyzed.

For example, to identify candidate autoantigens associated with MG, a protein sample from the muscle end-plate of a mature neuromuscular junction, at which the immune-mediated loss of acetylcholine receptors characteristic of MG occurs, might be used. First, the protein sample would be passed over the column containing immunoglobulins isolated from a healthy individual. The unbound proteins are then passed over the column containing immunoglobulins isolated from a patient suffering from MG. All proteins bound to the second column are candidate autoantigens that are then eluted from the column and used in further analysis, such as, for example, mass spectrometry, to identify each isolated protein.

By this method, hsp60 and hsp90 were identified as two novel candidate autoantigens in patients with MG. ELISA data demonstrated that patients with early stage MG (defined as stage I or stage IIa) lacking autoantibodies that specifically bind the AChR have autoantibodies that specifically bind hsp60 and hsp90. Thus assaying for the presence of such autoantibodies provides a novel method of diagnosing MG, particularly in patients at early stages of the disease who lack autoantibodies for AChR, the autoantigen most commonly associated with the disease (see, e.g., FIG. 5).

Candidate autoantigens may also be identified by other methods, such as screening cDNA expression libraries, or by subtractive phage display. To identify possible autoantigens by these methods, phage display or other protein expression libraries are constructed using mRNA isolated from an organ, tissue, or cell type involved in the etiology or progression of MG (e.g., the muscle end-plate of a mature neuromuscular junction). Such libraries are then screened with immunoglobulins purified from serum samples obtained from individuals suffering from the autoimmune disorder of interest, and the results compared to those obtained using immunoglobulins purified from serum samples obtained from healthy individuals.

There are many additional variations on the standard autoantigen screening protocols, in addition to those presented above. One of ordinary skill in the art will select the appropriate protocol to use, depending on the autoimmune disease being studied, the source of the biological sample to be screened for candidate autoantigens, and any other relevant experimental parameters. These and many other permutations and possibilities will be readily apparent to those of ordinary skill in the art, and are considered as equivalents within the scope of the instant invention.

1. Heat-Shock Proteins

Organisms respond to sudden increases in temperature or other forms of environmental stress by synthesizing a small set of evolutionarily conserved proteins called heat-shock proteins. Both the nature of the heat-shock response and the amino acid sequences of the various heat-shock protein family members are highly-conserved throughout evolution. For example, prokaryotic and eukaryotic heat-shock protein 70 (hsp70) are approximately 50% identical at the amino acid level. Parsell et al., "The function of heat-shock proteins in stress tolerance: degradation and reactivation of damaged proteins," Ann. Rev. Genet. 27:437-496 (1993). Individual members of the heat-shock protein family play different roles in protecting organisms from environmental stresses.

a. The 60 kD Heat-Shock Protein

The 60 kD heat-shock protein ("hsp60") is found primarily in the mitochondrial matrix, where it accounts for approximately 1% of all mitochondrial matrix protein. Parsell et al., supra at 465. Human hsp60 (SEQ ID NO:1) shares approximately 60% amino acid sequence identity with its *E. coli* homolog, GroEL. Id. Both proteins share a common oligomeric structure, consisting of a single, seven-membered ring, but sometimes observed as a "double doughnut" of two seven-membered rings. Id. Hsp60 has an ATPase activity that increases with increasing temperature; the binding of ATP induces a significant conformational change in structure of the oligomer. Id.

Unlike some other heat-shock protein family members, hsp60 functions at normal temperatures. Id. at 465-66. It is essential for growth at all temperatures Id. Hsp60 binds unfolded or denatured proteins with high affinity and promotes their proper folding. Id. Denatured substrates begin to acquire elements of secondary structure while bound to hsp60, though formation of more complex structural elements is inhibited. Id.

b. The 90 kD Heat-Shock Protein

The 90 kD heat-shock protein ("hsp90") has been found in the cytoplasm and nucleus of all eukaryotes examined so far, though no organellar species have yet been identified. Parsell et al., supra at 470. There are two major cytoplasmic isoforms of hsp90: hsp90α, the inducible, major form (SEQ ID NO:2); and hsp90μ, the constitutively expressed, minor form (SEQ ID NO:3). Sreedhar et al., "Hsp90 isoforms: functions, expression and clinical importance," *FEBS Letters* 562:11-15 (2004). Biochemical separation of the α and β isoforms is difficult, and so most experiments investigating the biological role of hsp90 have been performed using a mixture of both. Id.

Human hsp90α shares approximately 40% amino acid sequence identity with its *E. coli* homolog, HtpG. Parsell, supra. HtpG is moderately abundant at normal temperatures, and strongly induced by heat, but is not essential: deletion of the gene encoding it has no effect on growth at normal temperatures, and little effect at high temperatures. Id. In contrast, hsp90 is one of the most abundant proteins in eukaryotic cells, comprising 1-2% of total cellular protein under non-stress conditions. Deletion of the hsp90 gene in a eukaryote is lethal, suggesting that eukaryotic hsp90 has acquired a novel, essential function not present in its prokaryotic homolog. Sreedhar et al., supra; Parsell et al., supra.

Hsp90 interacts with many other cellular proteins, including casein kinase II, heme-regulated elF-2α kinase, various steroid hormone receptors, including estrogen, progesterone, androgen, glucocorticoid, and dioxin receptors, oncogenic tyrosine kinases of the src family, calmodulin, actin, and tubulin. Parsell et al., supra at 471. Experiments suggest that hsp90 plays a variety of roles in cell differentiation and development, ranging from regulation of muscle development to the regulation of early embryonic development and programmed cell death, or apoptosis. Sreedhar et al., supra, at 12. In addition, some evidence suggests that hsp90 expression is associated with several types of tumors, including pancreatic and breast, and with leukemia. Id. at 13. In addition, elevated transcription of hsp90β is associated with systemic lupus erythematosus, an autoimmune disorder characterized by autoantibodies directed to spliceosomal snRNP, Ro/La ribonuclear particle, histones, and/or native DNA. Id.

II. Kits for Diagnosing Autoimmune Disorders

The methods of the invention may be implemented in a diagnostic kit that incorporates one or more of the above techniques to detect autoantibodies that specifically bind at least one autoantigen characteristic of myasthenia gravis. For example, in one embodiment, the kit assays an amount of said autoantibody by Western blotting. In one aspect, the kit comprises multiple test strips on which aliquots of each of the two novel autoantigens of the invention, hsp60 and hsp90α/hsp90β, have been fixed.

In this embodiment, the kit further comprises control antibodies specific for each autoantigen, secondary antibodies directly or indirectly conjugated with horseradish peroxidase or any other agent that aids in the visualization of the autoantigen-autoantibody complex, and all necessary tubes, containers or reaction vessels, buffers and reagents required to perform the various blocking, washing, hybridization, and detection steps of a Western blot. The control antibody proteins can be provided in an appropriate buffer or solvent, or as a lyophilized powder. Similarly, the buffers and other reagents may be provided premixed, or in dry form that must be reconstituted by the user of the kit. Such a kit may contain other components, packaging, instructions, or other material to aid in the detection of autoantibodies.

In another embodiment, the kit assays an amount of said autoantibody by ELISA. In one aspect, the kit comprises multiple microtiter plates coated with each of the two novel autoantigens of the invention, hsp60 and hsp90α/hsp90β.

In this embodiment, the kit further comprises control antibodies specific for each autoantigen, secondary antibodies directly or indirectly conjugated with horseradish peroxidase or any other agent that aids in the visualization of the autoantigen-autoantibody complex, and all necessary tubes, containers or reaction vessels, buffers and reagents required to perform the various blocking, washing, hybridization, and detection steps of an ELISA. The control antibody proteins can be provided in an appropriate buffer or solvent, or as a lyophilized powder. Similarly, the buffers and other reagents may be provided premixed, or in dry form that must be reconstituted by the user of the kit. Such a kit may contain other components, packaging, instructions, or other material to aid the detection of the autoantibodies.

EXAMPLES

Example 1

Identification of Autoantibodies by Western Blot

Serum samples were obtained from 209 myasthenia gravis patients at Shin-Kong Hospital, Taiwan, Republic of China. The patients were divided into four groups based on their thymic pathology: thirty-seven patients displayed some degree of thymic atrophy; one hundred twenty-one patients had developed thymoma; forty patients displayed some degree of thymic hyperplasia; and eleven patients had an unknown thymic pathology. Seventy-six patients had Type I MG; eighty-one had Type IIa; thirty-eight had Type IIb, and fourteen patients had either Type III or Type IV MG. Negative controls used serum samples taken from fifty-four patients at Taichung Veterans General Hospital, all suffering from the unrelated disorder membranous glomerulonephritis (MGN), which is not autoimmune in origin.

HepG2/C3A cell lysates were separated on 10% SDS-PAGE gels loaded with 20 μg per lane of cell extract and 2 μg per lane of hsp60 or hsp90 protein. The samples were electrophoresed at 80V in the stacking gel and at 120V in the resolving gel. Fractionated proteins were transferred to PVDF using a TE70 Series Semi-dry Transfer Unit (Amersham Bioscience), according to the manufacturer's instructions. The transfer buffer was Towbin Buffer (1× is 25 mM Tris-HCl, pH=8.30, 192 mM glycine, and 20% (v/v) methanol).

The PVDF membranes were blocked in 5% (w/v) powdered non-fat milk in PBST buffer (80 mM $Na_2HPO_4$, 20 mM $NaH_2PO_4$, 100 mM NaCl, 0.05%-0.1% (v/v) Tween-20) for 1 hour at room temperature, or overnight at 4° C. The blocked membranes were then incubated in 5% (w/v) powdered non-fat milk in PBST buffer containing a 1:1000 dilution of patient serum for one hour at room temperature. Following incubation with the primary antibody, the membranes were washed with PBST. The membranes were then incubated for one hour at room temperature with the secondary antibody, an anti-human IgG labeled with horseradish peroxidase diluted 1:5000 in 5% (w/v) powdered non-fat milk in PBST buffer. The secondary antibody was horseradish peroxidase-conjugated mouse anti-human IgG specific for Fcγ (Jackson ImmunoResearch Laboratories, Inc.), purchased from Biosource International, of Camarillo, Calif., USA. Autoantibody binding to immobilized antigens was detected by enzyme-linked chemiluminescence using the ECL blotting substrate of Amersham Pharmacia Biotech, according to the manufacturer's instructions.

Figure 2:
FIG. 2 shows Western blots of cell lysates probed with serum from patients suffering from generalized myasthenia gravis according to the protocol of Example 1, identifying autoantibodies specific for heat-shock protein 90 (hsp90). These experiments did not distinguish between the alpha and beta isoforms of hsp90. Positive blots are indicated with a dot. Samples were taken from female patients with thymic hyperplasia (HF), male patients with thymic hyperplasia (HM), female patients with thymoma (TF), and male patients with thymoma (TM).
Figure 2:
Figure 2:
Figure 2:
Figure 2:
Figure 2:
Figure 2:
Figure 2:

The results of these experiments are shown in FIGS. 1 and 2. Samples were taken from female patients with thymic hyperplasia (HF), male patients with thymic hyperplasia (HM), female patients with thymoma (TF), and male patients with thymoma (TM). Samples positive for autoantibodies specific for hsp60 or hsp90 are indicated by a dot. These experiments demonstrate that many patients at later stages of MG have autoantibodies specific for hsp60 and hsp90.

Example 2

Identification of Autoantibodies by Enzyme-linked Immunosorbent Assay (ELISA)

Aliquots of the serum samples described in Example 1 above, were further evaluated by ELISA. Microwell ELISA plates (Corning Life Sciences, New York, N.Y., USA) were coated overnight at 4° C. with 0.2 μg of recombinant human hsp60 (purified from *E. coli*) or hsp90 (purified from *S. cerevisiae*) in 0.1 M $NaHCO_3$, pH 8.6. Both recombinant heat-shock proteins were purchased from Sigma-Aldrich Co. The coated plates were then washed with PBS three times for one minute each, and then incubated with 200 μl of blocking solution (5 mg/ml bovine serum albumin ("BSA") in PBST) at 37° C. for 1 hour. Each well was washed with PBST six times for one minute each. Next, the plates were incubated with patient serum diluted from 1:100 to 1:800 in blocking solution for 1 hour and 30 minutes at 37° C. After incubation with the primary antibody, the plates were again washed six times for one minute each with blocking solution, and then incubated with the secondary antibody, horseradish peroxidase-conjugated mouse anti-human IgG specific for Fcγ (Jackson ImmunoResearch Laboratories, Inc.) diluted 1:10,000 in PBST+5 mg/ml BSA, at room temperature for 1 hour. The plates were again washed six times with PBST+5 mg/ml BSA at room temperature, and developed by the addition of 100 μl of 3,3',5,5'-tetramethylbenzidine ("TMB") solution, prepared in 50 mM citrate phosphate. After the addition of the TMB solution, the plates were incubated for thirty minutes at room temperature, and then absorbance was measured at 450 nm with an MRX Microplate Reader (Dynex Technologies) according to the manufacturer's instructions.

Figure 3:
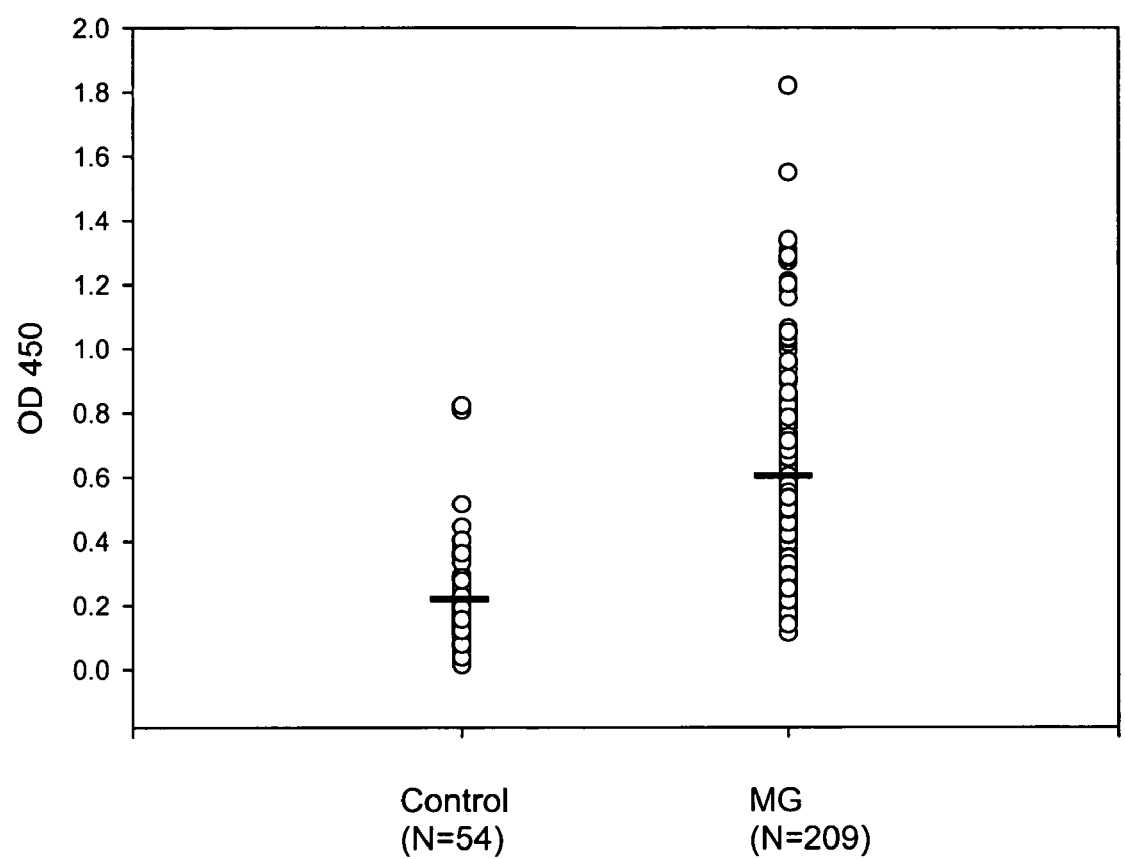
FIG. 3 shows the results of enzyme-linked immunosorbent assays (ELISAs) performed with serum from patients with generalized MG identifying hsp60, according to the protocol of Example 2. Bars indicate the mean $OD_{450}$ value.
Figure 4:
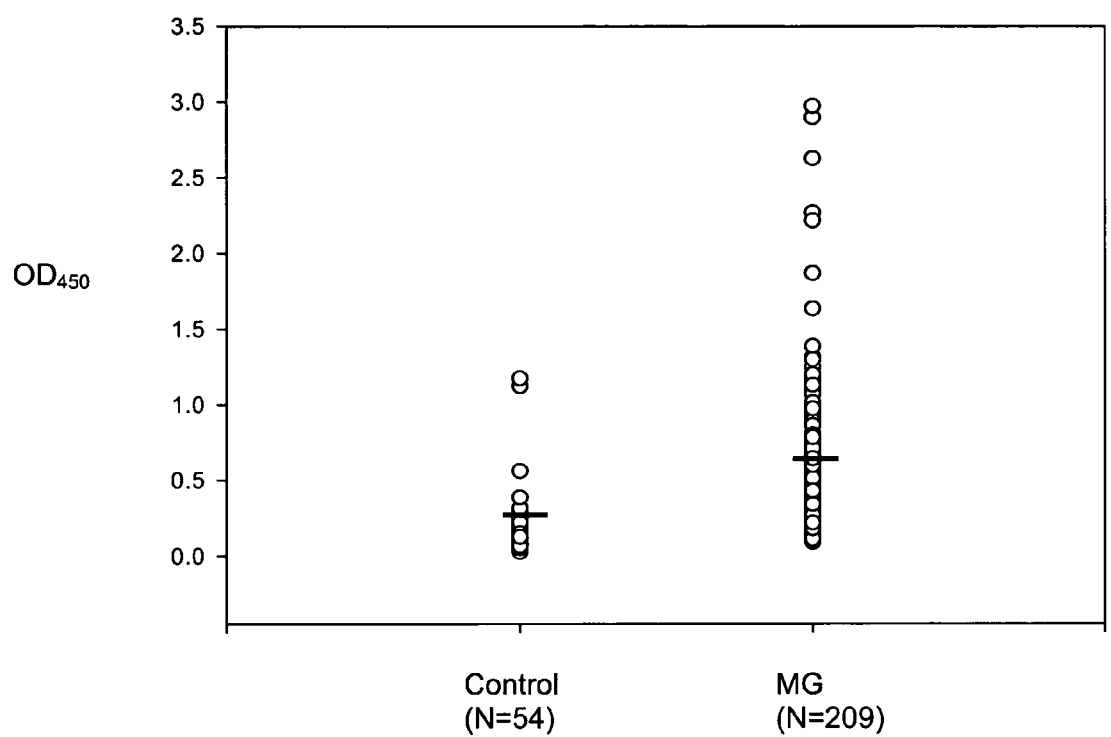
FIG. 4 shows the results of enzyme-linked immunosorbent assays (ELISAs) performed with serum from patients with generalized MG, identifying hsp90, according to the protocol of Example 2. Bars indicate the mean $OD_{450}$ value. These experiments did not distinguish between the alpha and beta isoforms of hsp90.

The results of these experiments are shown in FIGS. 3 (hsp60) and 4 (hsp90), which compare ELISA results from the control group to those from the MG group, which included patients at all stages of the disease. The average absorbance at 450 nm is indicated by a horizontal line. These experiments did not distinguish between the alpha and beta isoforms of hsp90. The data shows that patients at all stages of MG have autoantibodies specific for hsp60 and hsp90.

Table 1 shows that MG may be accurately diagnosed in patients with Type I or IIa MG that lack AChR autoantibodies by assaying for the presence of autoantibodies that specifically bind hsp60 or hsp90. Autoantibodies specific for hsp60 and hsp90 were assayed by ELISA in forty patients: twenty-four diagnosed with Type I MG and sixteen diagnosed with Type IIa MG. Assays were performed with the protocol described in Example 2. Absorbance readings were converted to protein concentrations by standard methods. The cutoff points were: (1) 0.2 nmol/L (AChR); (2) $OD_{0.450}=0.375$ (hsp60); and (3) $OD_{450}=0.232$ (hsp90). All forty patients lacked detectable AChR autoantibodies (columns labeled "AChR"). Twenty-eight patients had measurable levels of hsp60 autoantibodies (18 of 24 with Type I; 10 of 16 with Type IIa; columns labeled "Hsp60"). Thirty-three patients had measurable levels of hsp90 autoantibodies (21 of 24 with type I; 12 of 16 with type IIa; columns labeled "Hsp90").

TABLE 1

| Patient No. & MG Stage | AchR | AchR | Hsp60 | Hsp60 | Hsp90 | Hsp90 |
|---|---|---|---|---|---|---|
| I-1 | <0.2 | − | 0.539 | + | 0.609 | + |
| I-2 | <0.2 | − | 0.593 | + | 0.293 | + |
| I-3 | <0.2 | − | 0.328 | − | 0.467 | + |
| I-4 | <0.2 | − | 0.716 | + | 0.498 | + |
| I-5 | <0.2 | − | 1.063 | + | 1.088 | + |
| I-6 | <0.2 | − | 0.907 | + | 0.898 | + |
| I-7 | <0.2 | − | 0.484 | + | 0.376 | + |
| I-8 | <0.2 | − | 0.724 | + | 0.644 | + |
| I-9 | <0.2 | − | 0.608 | + | 0.539 | + |
| I-10 | <0.2 | − | 0.61 | + | 0.495 | + |
| I-11 | <0.2 | − | 0.96 | + | 1.156 | + |
| I-12 | <0.2 | − | 0.412 | + | 0.365 | + |
| I-13 | <0.2 | − | 0.771 | + | 0.678 | + |
| I-14 | <0.2 | − | 0.769 | + | 0.743 | + |
| I-15 | <0.2 | − | 0.321 | − | 0.196 | − |
| I-16 | <0.2 | − | 0.623 | + | 0.632 | + |
| I-17 | <0.2 | − | 0.197 | − | 0.246 | + |
| I-18 | <0.2 | − | 0.309 | − | 0.236 | + |
| I-19 | <0.2 | − | 0.476 | + | 0.398 | + |
| I-20 | <0.2 | − | 0.708 | + | 0.175 | − |
| I-21 | <0.2 | − | 0.293 | − | 0.344 | + |
| I-22 | <0.2 | − | 0.711 | + | 0.708 | + |
| I-23 | <0.2 | − | 0.251 | − | 0.217 | − |
| I-24 | <0.2 | − | 0.535 | + | 0.34 | + |
| IIa-1 | <0.2 | − | 0.811 | + | 2.626 | + |
| IIa-2 | <0.2 | − | 0.542 | + | 0.497 | + |
| IIa-3 | <0.2 | − | 0.306 | − | 0.306 | + |
| IIa-4 | <0.2 | − | 0.498 | + | 0.324 | + |
| IIa-5 | <0.2 | − | 0.406 | + | 0.261 | + |
| IIa-6 | <0.2 | − | 0.169 | − | 0.162 | − |
| IIa-7 | <0.2 | − | 0.734 | + | 0.75 | + |
| IIa-8 | <0.2 | − | 0.313 | − | 0.226 | − |
| IIa-9 | <0.2 | − | 0.776 | + | 1.199 | + |
| IIa-10 | <0.2 | − | 0.214 | − | 0.106 | − |
| IIa-11 | <0.2 | − | 1.201 | + | 0.918 | + |
| IIa-12 | <0.2 | − | 0.193 | − | 0.138 | − |
| IIa-13 | <0.2 | − | 0.351 | − | 0.258 | + |
| IIa-14 | <0.2 | − | 0.552 | + | 0.8 | + |
| IIa-15 | <0.2 | − | 0.498 | + | 0.642 | + |
| IIa-16 | <0.2 | − | 1.051 | + | 0.783 | + |

Figure 5:
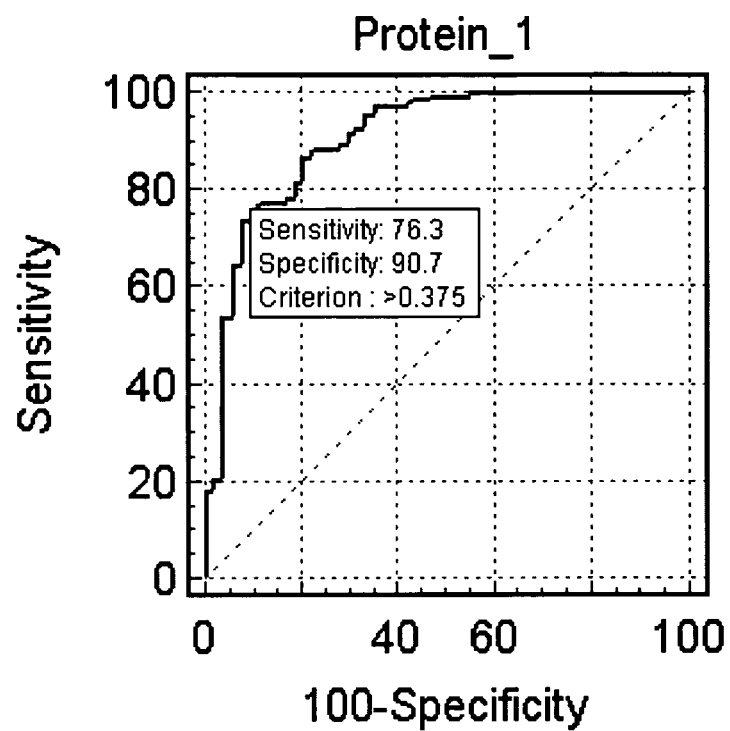
FIG. 5 shows the ability of the diagnostic methods of the invention correctly to categorize patients with MG as test-positive and those without as test-negative. Test-positive patients have autoantibodies that specifically bind hsp60 ("protein_1") and/or hsp90 ("protein_2"), while test-negative patients lack hsp60- and hsp90-specific autoantibodies.
Figure 5:
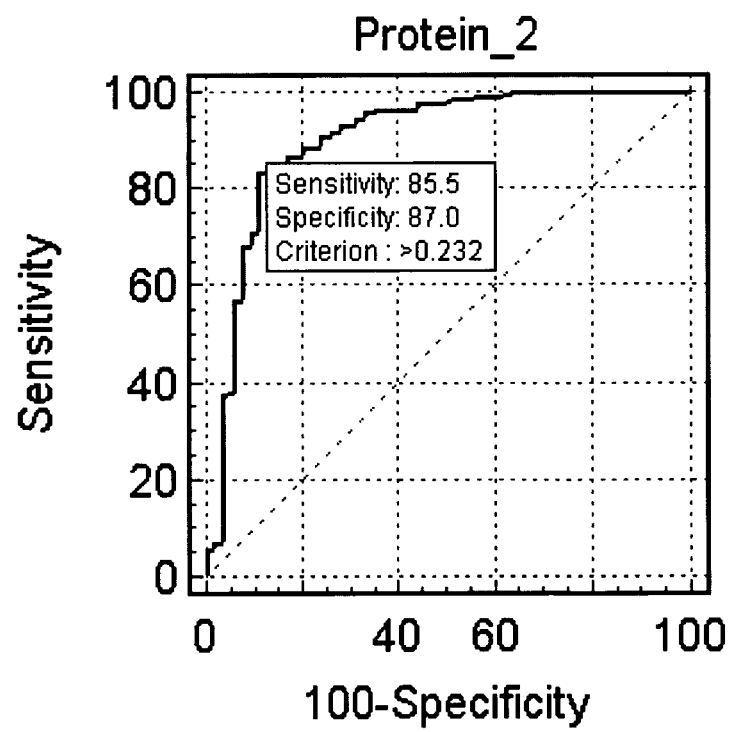

FIG. 5 shows that the methods of the invention provide for "sensitive" and "specific" diagnosis of MG. "Sensitivity" measures the percentage of patients diagnosed with MG who tested positive for autoantibodies that specifically bind either hsp60 ("Protein_1") or hsp90 ("Protein_2"). HENNEKENS ET AL., EPIDEMIOLOGY IN MEDICINE 331-335 (1ST ED. 1987). "Specificity" measures the percentage of patients who did not have MG who tested negative for either hsp60 ("Protein_1") or hsp90 ("Protein_2") autoantibodies. Id. This experiment demonstrates that, of patients diagnosed with ocular (Type I) or mild, generalized (Type IIa) MG lacking autoantibodies that specifically bind the AChR, 76% have autoantibodies that specifically bind hsp60 and 86% have autoantibodies that specifically bind hsp90. In addition, 91% of patients without MG tested negative for hsp60 autoantibodies, and 86% of patients without MG tested negative for hsp90 autoantibodies.

Table 2 shows that assaying for autoantibodies that specifically bind hsp60, hsp90, hsp60+hsp90, AChR+hsp60, or AChR+hsp90, provides a more sensitive method of identifying patients with stage I (ocular) MG than by assaying for autoantibodies specific for AChR alone. The data summarized in Table 2 was obtained from seventy-three patients with stage I MG using the ELISA assay and cutoff values as discussed above for Table 1.

TABLE 2

| Autoantigen(s) | Sensitivity for patients with stage I MG (%) |
| --- | --- |
| AChR | 67.1 |
| Hsp60 | 78.1 |
| Hsp90 | 86.3 |
| Hsp60 + Hsp 90 | 98.6 |
| AChR + Hsp60 | 91.7 |
| AChR + Hsp90 | 95.9 |

Thus assaying for the presence of hsp60 and/or hsp90 autoantibodies provides a novel, sensitive, and specific method of diagnosing MG, particularly in patients at early stages of the disease lacking autoantibodies for AChR, the clinical marker most commonly associated with the disease.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent that any general dictionary, technical dictionary, or the material incorporated by reference contradicts or is inconsistent with this specification, the specification will supersede any such material. The citation of any references herein is not an admission that such references are prior art to the present invention.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

REFERENCES

COTRAN ET AL., PATHOLOGIC BASIS OF DISEASE 211-212, 1289 (W.B. Saunders Co., Philadelphia, Pa.; 6th ed. 1999).

HENNEKENS ET AL., EPIDEMIOLOGY IN MEDICINE 331-335 (1ST ED. 1987).

Hoch et al., "Auto-antibodies to the receptor tyrosine kinase MsSK in patients with myasthenia gravis without acetylcholine receptor antibodies," Nature Med. 7(3):365-368 (2001).

Howard, "Myasthenia gravis: a summary."

KIRKEGAARD & PERRY LABORATORIES, INC., TECHNICAL GUIDE FOR ELISA 9-21 (2003).

Luo et al., "Regulation of AChR clustering by dishevelled interacting with MuSK and PAK1," Neuron 35:489-505 (2002).

Morgan et al., "The Matrix Effects on Kinetic Rate Constants of Antibody-Antigen Interactions Reflect Solvent Viscosity," J. Immunol. Meth. 217:51-60 (1998).

Tuen, C., "Myasthen ia Gravis."

Osserman, K. E. and Genkins, G., "Studies in myasthenia gravis: review of a twenty-year experience in over 1200 patients," Mt Sinai J. Med. 38(6):497-537 (1971).

Parsell et al., "The function of heat-shock proteins in stress tolerance: degradation and reactivation of damaged proteins," Ann Rev. Genet. 27:437-496 (1993).

Ragheb et al., "Myasthenia gravis patients, but not healthy subjects, recognize epitopes that are unique to the ε-subunit of the acetylcholine receptor," J. Neuroimmunol. 159:137-145 (2005).

Richman et al., "Treatment of autoimmune myasthenia gravis," Neurol. 61:1652-1661 (2003).

Robinson et al., "Autoantigen microarrays for multiplex characterization of autoantibody responses," Nature Med. 8(3):295-301 (2002).

Roxanis et al., "Thymic myoid cells and germinal center formation in myasthenia gravis; possible roles in pathogenesis," J. Neuroimmunol. 125:185-197 (2002).

SAMBROOK ET AL., 3 MOLECULAR CLONING: A LABORATORY MANUAL A8.40-A8.45 and A8.52-A8.55 (Cold Spring Harbor Laboratories Press, Cold Spring Harbor, N.Y., 3d ed. 2001).

Scofield, "Autoantibodies as predictors of disease," Lancet 363:1544-1546 (2004).

Somnier, "Increasing incidence of late-onset anti-AChR antibody-seropositive myasthenia gravis," Neurol. 65:928-930 (2005).

Sreedhar et al., "Hsp90 isoforms: functions, expression and clinical importance," FEBS Letters 562:11-15 (2004).

Zhuang et al., "Measurement of Association Rate Constant of Antibody-Antigen Interaction in Solution Based on Enzyme-Linked Immunosorbent Assay," J. Biosci. Bioeng. 92(4):330-336 (2001).

What is claimed is:

1. A method of diagnosing myasthenia gravis in a subject suspected of having myasthenia gravis, the method comprising:
    (a) determining if the subject has one or more clinical symptoms associated with myasthenia gravis;
    (b) obtaining a biological sample from the subject; and
    (c) detecting the amount of Hsp60 autoantibodies or Hsp90 autoantibodies or of both in the biological sample, wherein
        said Hsp60 autoantibodies specifically bind heat-shock protein 60 (hsp60) (SEQ ID NO: 1), and
        said Hsp90 autoantibodies specifically bind heat-shock protein 90 (Hsp90),
    wherein the Hsp90 is Hsp90, alpha isoform (Hsp90α) (SEQ ID NO:2), or Hsp90, beta isoform (Hsp90β)(SEQ ID NO: 3), or both;
    (d) diagnosing whether the subject has myasthenia gravis by comparing the amount of Hsp60 autoantibodies or Hsp90 autoantibodies or of both in said sample to a cutoff value for each type of autoantibody,
    wherein the cutoff value for each type of autoantibody is determined from a number of individuals who do not have myasthenia gravis; and
    wherein the presence of at least one of said Hsp60 and Hsp90 autoantibodies in the biological sample above the cutoff indicates the subject has myasthenia gravis.

2. The method of claim 1, wherein said clinical symptoms are one or more of the following: ocular ptosis; diplopia; difficulty chewing, talking, swallowing, or breathing; chronic muscle fatigue or weakness; thymic atrophy; thymoma; and thymic hyperplasia.

3. The method of claim 2, wherein the biological sample is selected from serum, blood, plasma, saliva, amniotic fluid, synovial fluid, lacrimal fluid, milk, lymph, urine, and sweat.

4. The method of claim 3, wherein the autoantibodies are detected by one or more methods selected from:
    (a) Western blot; and
    (b) enzyme-linked immunosorbent assay (ELISA).

5. The method of claim 4, wherein the subject is a mammal.

6. The method of claim 5, wherein the mammal is a human.

7. The method of claim 5, wherein the mammal is a rodent.

8. The method of claim 7, wherein the rodent is a mouse.

9. The method of claim 7, wherein the rodent is a rat.

10. A method of diagnosing myasthenia gravis in a subject suspected of having myasthenia gravis, the method comprising:
    (a) determining if the subject has one or more clinical symptoms associated with myasthenia gravis;
    (b) obtaining a biological sample from the subject; and
    (c) detecting the amount of
        (i) at least one of Hsp60 autoantibodies and Hsp90 autoantibodies and
        (ii) AchR autoantibodies
    in the biological sample, wherein
        said Hsp60 autoantibodies specifically bind heat-shock protein 60 (hsp60) (SEQ ID NO:1)
        said Hsp90 autoantibodies specifically bind heat-shock protein 90 (hsp90),
    wherein the Hsp90 is Hsp90α (SEQ ID NO:2), or Hsp90β (SEQ ID NO:3), or both; and
    said AchR autoantibodies specifically bind nicotinic acetyicholine receptor (Ach R);
and
    (d) diagnosing whether the subject has myasthenia gravis by comparing the amount of
        (i) at least one of Hsp60 autoantibodies and Hsp90 autoantibodies and
        (ii) AchR autoantibodies in said sample to a cutoff value for each type of autoantibody,
    wherein the cutoff value for each type of autoantibody is determined from a number of individuals who do not have myasthenia gravis; and
    wherein the presence of
        (i) at least one of Hsp60 autoantibodies and Hsp90 autoantibodies and
        (ii) AchR autoantibodies in the biological sample above the cutoff indicates the subject has myasthenia gravis.

11. The method of claim 10, wherein said clinical symptoms are one or more of the following: ocular ptosis; diplopia; difficulty chewing, talking, swallowing, or breathing; chronic muscle fatigue or weakness; thymic atrophy; thymoma; and thymic hyperplasia.

* * * * *

UNITED STATES PATENT AND TRADEMARK OFFICE
CERTIFICATE OF CORRECTION

| | |
|---|---|
| PATENT NO. | : 7,807,378 B2 |
| APPLICATION NO. | : 11/321516 |
| DATED | : October 5, 2010 |
| INVENTOR(S) | : Tzu-Ling Tseng et al. |

It is certified that error appears in the above-identified patent and that said Letters Patent is hereby corrected as shown below:

Claim 10, col. 28, line 33, "acetyicholine" should read -- acetylcholine --.

Signed and Sealed this
Eleventh Day of January, 2011

David J. Kappos
*Director of the United States Patent and Trademark Office*

SEQUENCE LISTING

<160> NUMBER OF SEQ ID NOS: 3

<210> SEQ ID NO 1

<211> LENGTH: 573
<212> TYPE: PRT
<213> ORGANISM: Homo sapiens

<400> SEQUENCE: 1

```
Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
        275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
            340                 345                 350

Asp Asp Ala Met Leu Leu Lys Gly Lys Gly Asp Lys Ala Gln Ile Glu
        355                 360                 365

Lys Arg Ile Gln Glu Ile Ile Glu Gln Leu Asp Val Thr Thr Ser Glu
    370                 375                 380

Tyr Glu Lys Glu Lys Leu Asn Glu Arg Leu Ala Lys Leu Ser Asp Gly
```

```
                385                 390                 395                 400
Val Ala Val Leu Lys Val Gly Gly Thr Ser Asp Val Glu Val Asn Glu
                    405                 410                 415

Lys Lys Asp Arg Val Thr Asp Ala Leu Asn Ala Thr Arg Ala Ala Val
                420                 425                 430

Glu Glu Gly Ile Val Leu Gly Gly Cys Ala Leu Leu Arg Cys Ile
                435                 440                 445

Pro Ala Leu Asp Ser Leu Thr Pro Ala Asn Glu Asp Gln Lys Ile Gly
                450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                    485                 490                 495

Ser Ser Ser Glu Val Gly Tyr Asp Ala Met Ala Gly Asp Phe Val Asn
                500                 505                 510

Met Val Glu Lys Gly Ile Ile Asp Pro Thr Lys Val Val Arg Thr Ala
                515                 520                 525

Leu Leu Asp Ala Ala Gly Val Ala Ser Leu Leu Thr Thr Ala Glu Val
                530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Met Phe
                    565                 570

<210> SEQ ID NO 2
<211> LENGTH: 732
<212> TYPE: PRT
<213> ORGANISM: Homo sapiens

<400> SEQUENCE: 2

Met Pro Glu Glu Thr Gln Thr Gln Asp Gln Pro Met Glu Glu Glu Glu
1               5                   10                  15

Val Glu Thr Phe Ala Phe Gln Ala Glu Ile Ala Gln Leu Met Ser Leu
                20                  25                  30

Ile Ile Asn Thr Phe Tyr Ser Asn Lys Glu Ile Phe Leu Arg Glu Leu
                35                  40                  45

Ile Ser Asn Ser Ser Asp Ala Leu Asp Lys Ile Arg Tyr Glu Ser Leu
            50                  55                  60

Thr Asp Pro Ser Lys Leu Asp Ser Gly Lys Glu Leu His Ile Asn Leu
65              70                  75                  80

Ile Pro Asn Lys Gln Asp Arg Thr Leu Thr Ile Val Asp Thr Gly Ile
                85                  90                  95

Gly Met Thr Lys Ala Asp Leu Ile Asn Asn Leu Gly Thr Ile Ala Lys
                100                 105                 110

Ser Gly Thr Lys Ala Phe Met Glu Ala Leu Gln Ala Gly Ala Asp Ile
                115                 120                 125

Ser Met Ile Gly Gln Phe Gly Val Gly Phe Tyr Ser Ala Tyr Leu Val
            130                 135                 140

Ala Glu Lys Val Thr Val Ile Thr Lys His Asn Asp Asp Glu Gln Tyr
145             150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
                180                 185                 190
```

```
Asp Gln Thr Glu Tyr Leu Glu Glu Arg Arg Ile Lys Glu Ile Val Lys
    195                 200                 205
Lys His Ser Gln Phe Ile Gly Tyr Pro Ile Thr Leu Phe Val Glu Lys
    210                 215                 220
Glu Arg Asp Lys Glu Val Ser Asp Glu Ala Glu Glu Lys Glu Asp
225                 230                 235                 240
Lys Glu Glu Glu Lys Glu Lys Glu Glu Lys Glu Ser Glu Asp Lys Pro
                245                 250                 255
Glu Ile Glu Asp Val Gly Ser Asp Glu Glu Glu Glu Lys Lys Asp Gly
                260                 265                 270
Asp Lys Lys Lys Lys Lys Lys Ile Lys Glu Lys Tyr Ile Asp Gln Glu
            275                 280                 285
Glu Leu Asn Lys Thr Lys Pro Ile Trp Thr Arg Asn Pro Asp Asp Ile
        290                 295                 300
Thr Asn Glu Glu Tyr Gly Glu Phe Tyr Lys Ser Leu Thr Asn Asp Trp
305                 310                 315                 320
Glu Asp His Leu Ala Val Lys His Phe Ser Val Glu Gly Gln Leu Glu
                325                 330                 335
Phe Arg Ala Leu Leu Phe Val Pro Arg Arg Ala Pro Phe Asp Leu Phe
                340                 345                 350
Glu Asn Arg Lys Lys Lys Asn Asn Ile Lys Leu Tyr Val Arg Arg Val
            355                 360                 365
Phe Ile Met Asp Asn Cys Glu Glu Leu Ile Pro Glu Tyr Leu Asn Phe
        370                 375                 380
Ile Arg Gly Val Val Asp Ser Glu Asp Leu Pro Leu Asn Ile Ser Arg
385                 390                 395                 400
Glu Met Leu Gln Gln Ser Lys Ile Leu Lys Val Ile Arg Lys Asn Leu
                405                 410                 415
Val Lys Lys Cys Leu Glu Leu Phe Thr Glu Leu Ala Glu Asp Lys Glu
                420                 425                 430
Asn Tyr Lys Lys Phe Tyr Glu Gln Phe Ser Lys Asn Ile Lys Leu Gly
            435                 440                 445
Ile His Glu Asp Ser Gln Asn Arg Lys Lys Leu Ser Glu Leu Leu Arg
        450                 455                 460
Tyr Tyr Thr Ser Ala Ser Gly Asp Glu Met Val Ser Leu Lys Asp Tyr
465                 470                 475                 480
Cys Thr Arg Met Lys Glu Asn Gln Lys His Ile Tyr Tyr Ile Thr Gly
                485                 490                 495
Glu Thr Lys Asp Gln Val Ala Asn Ser Ala Phe Val Glu Arg Leu Arg
                500                 505                 510
Lys His Gly Leu Glu Val Ile Tyr Met Ile Glu Pro Ile Asp Glu Tyr
            515                 520                 525
Cys Val Gln Gln Leu Lys Glu Phe Glu Gly Lys Thr Leu Val Ser Val
        530                 535                 540
Thr Lys Glu Gly Leu Glu Leu Pro Glu Asp Glu Glu Lys Lys Lys
545                 550                 555                 560
Gln Glu Glu Lys Lys Thr Lys Phe Glu Asn Leu Cys Lys Ile Met Lys
                565                 570                 575
Asp Ile Leu Glu Lys Lys Val Glu Lys Val Val Val Ser Asn Arg Leu
            580                 585                 590
Val Thr Ser Pro Cys Cys Ile Val Thr Ser Thr Tyr Gly Trp Thr Ala
        595                 600                 605
Asn Met Glu Arg Ile Met Lys Ala Gln Ala Leu Arg Asp Asn Ser Thr
```

-continued

```
                610                 615                 620
Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
                645                 650                 655

Lys Ser Val Lys Asp Leu Val Ile Leu Leu Tyr Glu Thr Ala Leu Leu
            660                 665                 670

Ser Ser Gly Phe Ser Leu Glu Asp Pro Gln Thr His Ala Asn Arg Ile
        675                 680                 685

Tyr Arg Met Ile Lys Leu Gly Leu Gly Ile Asp Glu Asp Pro Thr
690                 695                 700

Ala Asp Asp Thr Ser Ala Ala Val Thr Glu Glu Met Pro Pro Leu Glu
705                 710                 715                 720

Gly Asp Asp Asp Thr Ser Arg Met Glu Glu Val Asp
                725                 730

<210> SEQ ID NO 3
<211> LENGTH: 724
<212> TYPE: PRT
<213> ORGANISM: Homo sapiens

<400> SEQUENCE: 3

Met Pro Glu Glu Val His His Gly Glu Glu Val Glu Thr Phe Ala
1               5                   10                  15

Phe Gln Ala Glu Ile Ala Gln Leu Met Ser Leu Ile Ile Asn Thr Phe
                20                  25                  30

Tyr Ser Asn Lys Glu Ile Phe Leu Arg Glu Leu Ile Ser Asn Ala Ser
            35                  40                  45

Asp Ala Leu Asp Lys Ile Arg Tyr Glu Ser Leu Thr Asp Pro Ser Lys
        50                  55                  60

Leu Asp Ser Gly Lys Glu Leu Lys Ile Asp Ile Ile Pro Asn Pro Gln
65                  70                  75                  80

Glu Arg Thr Leu Thr Leu Val Asp Thr Gly Ile Gly Met Thr Lys Ala
                85                  90                  95

Asp Leu Ile Asn Asn Leu Gly Thr Ile Ala Lys Ser Gly Thr Lys Ala
            100                 105                 110

Phe Met Glu Ala Leu Gln Ala Gly Ala Asp Ile Ser Met Ile Gly Gln
        115                 120                 125

Phe Gly Val Gly Phe Tyr Ser Ala Tyr Leu Val Ala Glu Lys Val Val
    130                 135                 140

Val Ile Thr Lys His Asn Asp Asp Glu Gln Tyr Ala Trp Glu Ser Ser
145                 150                 155                 160

Ala Gly Gly Ser Phe Thr Val Arg Ala Asp His Gly Glu Pro Ile Gly
                165                 170                 175

Arg Gly Thr Lys Val Ile Leu His Leu Lys Glu Asp Gln Thr Glu Tyr
            180                 185                 190

Leu Glu Glu Arg Arg Val Lys Glu Val Val Lys Lys His Ser Gln Phe
        195                 200                 205

Ile Gly Tyr Pro Ile Thr Leu Tyr Leu Glu Lys Glu Arg Glu Lys Glu
    210                 215                 220

Ile Ser Asp Asp Glu Ala Glu Glu Glu Lys Gly Glu Lys Glu Glu Glu
225                 230                 235                 240

Asp Lys Asp Asp Glu Glu Lys Pro Lys Ile Glu Asp Val Gly Ser Asp
                245                 250                 255
```

-continued

```
Glu Glu Asp Asp Ser Gly Lys Asp Lys Lys Lys Thr Lys Lys Ile
            260                 265                 270

Lys Glu Lys Tyr Ile Asp Gln Glu Glu Leu Asn Lys Thr Lys Pro Ile
        275                 280                 285

Trp Thr Arg Asn Pro Asp Ile Thr Gln Glu Tyr Gly Glu Phe
    290                 295                 300

Tyr Lys Ser Leu Thr Asn Asp Trp Glu Asp His Leu Ala Val Lys His
305                 310                 315                 320

Phe Ser Val Glu Gly Gln Leu Glu Phe Arg Ala Leu Leu Phe Ile Pro
                325                 330                 335

Arg Arg Ala Pro Phe Asp Leu Phe Glu Asn Lys Lys Lys Asn Asn
                340                 345                 350

Ile Lys Leu Tyr Val Arg Arg Val Phe Ile Met Asp Ser Cys Asp Glu
        355                 360                 365

Leu Ile Pro Glu Tyr Leu Asn Phe Ile Arg Gly Val Val Asp Ser Glu
    370                 375                 380

Asp Leu Pro Leu Asn Ile Ser Arg Glu Met Leu Gln Gln Ser Lys Ile
385                 390                 395                 400

Leu Lys Val Ile Arg Lys Asn Ile Val Lys Lys Cys Leu Glu Leu Phe
                405                 410                 415

Ser Glu Leu Ala Glu Asp Lys Glu Asn Tyr Lys Lys Phe Tyr Glu Ala
                420                 425                 430

Phe Ser Lys Asn Leu Lys Leu Gly Ile His Glu Asp Ser Thr Asn Arg
        435                 440                 445

Arg Arg Leu Ser Glu Leu Leu Arg Tyr His Thr Ser Gln Ser Gly Asp
    450                 455                 460

Glu Met Thr Ser Leu Ser Glu Tyr Val Ser Arg Met Lys Glu Thr Gln
465                 470                 475                 480

Lys Ser Ile Tyr Tyr Ile Thr Gly Glu Ser Lys Glu Gln Val Ala Asn
                485                 490                 495

Ser Ala Phe Val Glu Arg Val Arg Lys Arg Gly Phe Glu Val Val Tyr
            500                 505                 510

Met Thr Glu Pro Ile Asp Glu Tyr Cys Val Gln Gln Leu Lys Glu Phe
            515                 520                 525

Asp Gly Lys Ser Leu Val Ser Val Thr Lys Glu Gly Leu Glu Leu Pro
530                 535                 540

Glu Asp Glu Glu Glu Lys Lys Lys Met Glu Glu Ser Lys Ala Lys Phe
545                 550                 555                 560

Glu Asn Leu Cys Lys Leu Met Lys Glu Ile Leu Asp Lys Lys Val Glu
                565                 570                 575

Lys Val Thr Ile Ser Asn Arg Leu Val Ser Ser Pro Cys Cys Ile Val
            580                 585                 590

Thr Ser Thr Tyr Gly Trp Thr Ala Asn Met Glu Arg Ile Met Lys Ala
            595                 600                 605

Gln Ala Leu Arg Asp Asn Ser Thr Met Gly Tyr Met Met Ala Lys Lys
    610                 615                 620

His Leu Glu Ile Asn Pro Asp His Pro Ile Val Glu Thr Leu Arg Gln
625                 630                 635                 640

Lys Ala Glu Ala Asp Lys Asn Asp Lys Ala Val Lys Asp Leu Val Val
                645                 650                 655

Leu Leu Phe Glu Thr Ala Leu Leu Ser Ser Gly Phe Ser Leu Glu Asp
                660                 665                 670

Pro Gln Thr His Ser Asn Arg Ile Tyr Arg Met Ile Lys Leu Gly Leu
```

-continued

```
            675                 680                 685
Gly Ile Asp Glu Asp Glu Val Ala Ala Glu Glu Pro Asn Ala Ala Val
        690                 695                 700
Pro Asp Glu Ile Pro Pro Leu Glu Gly Asp Glu Asp Ala Ser Arg Met
705                 710                 715                 720
Glu Glu Val Asp
```